United States Patent [19]

Bettesworth et al.

[11] Patent Number: 5,109,004
[45] Date of Patent: Apr. 28, 1992

[54] PYRIMIDINE

[75] Inventors: Nicola J. Bettesworth, Camberley; Maureen Smith, Bucks; Trevor R. Perrior, Barkham; Alan J. Whittle, Twyford; Alfred G. Williams, Binfield; Donn W. Moseley, Reading, all of England

[73] Assignee: Imperial Chemical Industries PLC, London, England

[21] Appl. No.: 506,842

[22] Filed: Apr. 10, 1990

[30] Foreign Application Priority Data

Apr. 17, 1989 [GB] United Kingdom ............ 8908649
Oct. 26, 1989 [GB] United Kingdom ............ 8924126

[51] Int. Cl.$^5$ .................. C07D 251/10; A01N 43/54
[52] U.S. Cl. ........................ 514/269; 514/270; 514/272; 514/274; 544/301; 544/311; 544/312; 544/316; 544/317; 544/319; 544/320; 544/321; 544/296
[58] Field of Search ........... 544/301, 311, 312, 316, 544/317, 319, 320, 321; 514/269, 270

[56] References Cited

U.S. PATENT DOCUMENTS 4,617,316 10/1986 Plummer ...................... 514/438

OTHER PUBLICATIONS

Chemical Abstracts, vol. 64, 1966, Abstract No. 2084g, Columbus, Ohio, US, p. 2085, Y. Ashani et al., "Preparation and Properties of some halomethylpyrimidines".

Primary Examiner—John M. Ford
Attorney, Agent, or Firm—Cushman, Darby & Cushman

[57] ABSTRACT

A phenyl substituted heterocyclic compound of formula (I):

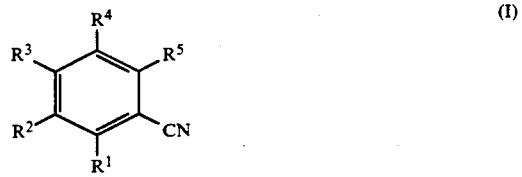

wherein $R^1$ is optionally substituted pyridone, thiopyridone, pyrimidinthione, pyrimidinone, pyrazole, imidazole or triazole group; $R^2$ is hydrogen, halogen, haloalkyl, nitro or cyano; $R^3$ and $R^5$ are independently selected from hydrogen, halogen, alkyl or cycloalkyl; $R^4$ is halogen, haloalkyl, haloalkoxy or $S(O)_nR^6$ where $R^6$ is alkyl, haloalkyl or cycloalkyl and n is 0, 1 or 2; having insecticidal activity.

7 Claims, No Drawings

PYRIMIDINE

The present invention relates to novel phenyl substituted heterocyclic compounds which have insecticidal activity, to processes for their preparation and to their use as insecticides.

According to the present invention there is provided an insecticidal compound of formula (I):

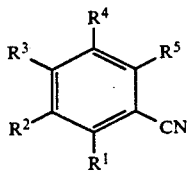

wherein $R^1$ is optionally substituted pyridone, thiopyridone, pyrimidinthione, pyrimidinone, pyrazole, imidazole or triazole group; $R^2$ is hydrogen, halogen, haloalkyl, nitro or cyano; $R^3$ and $R^5$ are independently selected from hydrogen, halogen, alkyl or cycloalkyl; $R^4$ is halogen, haloalkyl, haloalkoxy or $S(O)_nR^6$ where $R^6$ is alkyl, haloalkyl or cycloalkyl and n is 0, 1 or 2.

The term "alkyl" is used herein includes straight or branched chain alkyl groups, preferably containing up to 6 carbon atoms. This applies also to alkyl moieties contained in "haloalkyl" groups. The term "cycloalkyl" used herein refers to a carbocyclic ring suitably having from 3 to 10 and preferably from 3 to 7 carbon atoms in the ring. The cycloalkyl group is preferably cyclopropyl.

Suitable halogen groups, $R^2$, $R^3$, $R^4$ and $R^5$ include fluorine, chlorine, bromine or iodine.

Suitable haloalkyl groups for $R^2$, $R^4$ and $R^6$ are $C_1$-$C_4$ alkyl groups substituted with chlorine, fluorine, bromine or iodine. Such groups may include di- and trihalomethyl groups in particular trifluoromethyl, and pentahaloethyl groups, in particular pentafluoroethyl. Such groups may also include two or more different halogens.

Suitable haloalkoxy groups for $R^4$ include $C_1$-$C_4$ haloalkoxy groups, substituted with fluorine, chlorine, bromine, or iodine. Such groups may also include two or more different halogens.

Preferably $R^4$ is trifluoromethyl, pentafluoroethyl trifluoromethylthio, iodine, bromine, chlorine, trifluoromethoxy or methylthio.

Preferably $R^2$ is fluorine, chlorine, bromine, cyano, trifluoromethyl.

Preferably $R^3$ and $R^5$ are hydrogen

An example of group $R^1$ is a group of sub-formula (a):

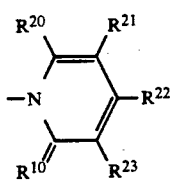

where $R^{10}$ is oxygen or sulphur; $R^{20}$ is hydrogen, halogen, optionally substituted amino, alkyl optionally substituted by halogen, alkoxy optionally substituted by halogen, and 25 thioalkoxy optionally substituted by halogen; $R^{21}$ is hydrogen, halogen, optionally substituted alkyl, optionally substituted alkoxy, optionally substituted thioalkoxy, cyano, nitro, optionally substituted oximino, optionally substituted alkenyl, optionally substituted aryloxy, optionally substituted amino or $S(O)_nR^6$ wherein n and $R^6$ are as hereinbefore defined; $R^{22}$ is hydrogen, or alkyl optionally substituted by halogen, lower alkenyl optionally substituted by halogen or $CO_2R^{37}$ wherein $R^{37}$ is alkyl optionally substituted by halogen; and $R^{23}$ is a group $R^{20}$ as defined above or a cyano or nitro group.

The term "alkenyl" used herein includes groups having from 2 to 6 carbon atoms, preferably 2 or 3 carbon atoms. The term "aryl" includes phenyl.

Examples of $R^{21}$ include hydrogen, halo, lower alkyl optionally substituted by halo or hydroxy; cyano; nitro; oximino optionally substituted by lower alkyl, aryl, lower alkenyl or aralkyl wherein the aryl portion is optionally substituted with halogen or nitro; lower alkenyl optionally substituted by halogen or cyano; amino; or $S(O)_nR^6$ wherein n and $R^6$ are as hereinbefore defined.

Specific examples of $R^{21}$ include hydrogen, iodine, methyl, hydroxymethyl, chloromethyl, difluoromethyl, dichloromethyl, thiomethyl, ethoxyimino, t-butyloximino, p-nitrobenzyloxyimino, phenoxyimino, pentafluorobenzyloximino, prop-2-enyloxyimino, 2,2-dichloroethenyl, 2-cyanoethenyl, ethynyl or $S(O)CF_3$.

Preferably $R^{21}$ is hydrogen, cyano, trifluoromethyl or pentafluoroethyl.

Suitable groups $R^{22}$ include halo(lower)alkyl, branched chain lower alkyl, halo(lower)alkenyl, or a lower carboxylic ester group.

Examples of suitable groups $R^{22}$ include trifluoromethyl, pentafluoroethyl, 2,2-di-bromoethenyl, ethoxycarbonyl and tert-butyl.

A further example of the group $R^1$ is a group of sub-formula (b):

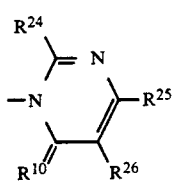

where $R^{10}$ is oxygen or sulphur; $R^{24}$ is hydrogen, halogen, $NR^7R^8$, $S(O)_nR^6$, alkyl or cycloalkyl wherein $R^7$ and $R^8$ are independently selected from hydrogen, alkyl or cycloalkyl; $R^{25}$ is halo, nitro, haloalkyl, haloalkoxy or $S(O)_nR^6$; and $R^{26}$ is hydrogen, alkyl, halogen, cyano, hydroxyalkyl, alkoxy, $S(O)_nR^6$, haloalkylthio, $NR^{11}R^{12}$, formyl, nitro or haloalkyl.

Suitable halogen groups for $R^{24}$, $R^{25}$ and $R^{26}$ include fluoro, chloro, bromo or iodine.

Suitable haloalkyl groups $R^{25}$, $R^{26}$ and $R^6$ include di- and trihalomethyl groups, in particular trifluoromethyl and pentahaloethyl groups such as pentafluoroethyl.

Preferably $R^{25}$ is trifluoromethyl or pentafluoroethyl.
Preferably $R^{24}$ and/or $R^{26}$ are hydrogen.

A further group of compounds of formula $R^1$ are compounds of sub-group (c):

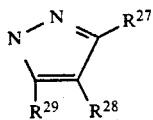

wherein R$^{27}$ is hydrogen, alkyl, haloalkyl, cyano, nitro, halogen, NR$^{11}$R$^{12}$ wherein R$^{11}$ and R$^{12}$ are independently selected from hydrogen or alkyl optionally substituted by C$_{2-5}$ alkoxycarbonyl, or cycloalkyl; is halogen; cyano; nitro; cycloalkyl; C$_{2-6}$ alkenyl; thiocyanato; sulphamoyl or carbamoyl either of which may be substituted with one or two alkyl groups; C$_{2-7}$ alkoxycarbonyl; C$_{2-7}$ alkanoyl; alkyl; haloalkyl; or S(O)$_n$R$^6$ where n and R$^6$ are as hereinbefore defined; R$^{29}$ is hydrogen; NR$^{11}$R$^{12}$ wherein R$^{11}$ and R$^{12}$ are independently selected from hydrogen or alkyl optionally substituted by C$_{2-5}$ alkoxycarbonyl, cycloalkyl, formyl, C$_{2-7}$ alkanoyl, C$_{4-7}$ cycloalkylcarbonyl, C$_{2-7}$ alkoxycarbonyl, C$_{2-7}$ haloalkoxycarbonyl or R$^{11}$ and R$^{12}$ together with the nitrogen to which they are attached form a cyclic imide optionally substituted by halogen; C$_{1-4}$ alkylsulphenylamino; alkoxymethyleneimino; halogen; alkyl; carboxy or salts thereof; alkylthio; alkylsulphinyl; haloalkylsulphinyl; alkylsulphonyl; haloalkylsulphonyl; trialkylmethylsilyl; cyano or nitro.

Any alkyl chains in the above groups may be straight or branched.

Suitable halogen atoms for R$^{27}$ are fluorine, chlorine, bromine or iodine.

Particularly preferred compounds are 1-(2-chloro-6-cyano-4-trifluoromethylphenyl)-3-dimethylamino-4-(trifluoromethylthio)-pyrazole and 1-(2-chloro-6-cyano-4-trifluoromethylphenyl)-4-(dichlorofluoromethylthio)pyrazole.

A further group R$^1$ is a group of formula (d):

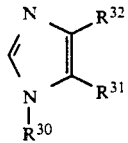

wherein R$^{30}$ is hydrogen or alkyl optionally substituted by alkoxy, alkylthio, alkylsulphinyl, alkylsulphonyl, cyano, carboxy or C$_{2-7}$ alkoxycarbonyl; R$^{31}$ and R$^{32}$ are independently selected from hydrogen; halogen; nitro; carboxy; cyano; C$_{2-7}$ alkoxycarbonyl; C$_{2-7}$ alkanoyl; carbamoyl or sulphamoyl either of which may be optionally substituted by one or two alkyl groups; amino optionally substituted by one or two groups selected from alkyl, C$_{2-7}$ alkoxycarbonyl and C$_{2-7}$ alkanoyl; alkyl; haloalkyl or S(O)$_n$R$^6$ where n and R$^6$ are as hereinbefore defined.

Preferably R$^{30}$ is hydrogen.

Preferably R$^{31}$ and R$^{32}$ are independently selected from cyano, trifluoromethyl, bromo or nitro.

Yet a further group R$^1$ is a group of sub-formula (e):

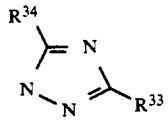

wherein R$^{33}$ is C$_{2-6}$ alkyl optionally substituted by halogen, alkoxy, alkylsulphonyl, alkoxycarbonyl or carbamoyl; cycloalkyl substituted by methyl; C$_{2-6}$ alkenyl; C$_{1-4}$ alkylsulphinyl or 2-methyl-1,3,-dithiolan-2-yl; and R$^{34}$ hydrogen; halogen; haloalkyl; alkoxyalkyl; C$_{2-6}$ alkenyloxyalkyl, methyl, alkylsulphinyl, alkylsulphonyl; phenyl; NR$^{13}$R$^{14}$ wherein R$^{13}$ and R$^{14}$ are independently selected from hydrogen, alkyl, alkoxy, acyl such as acetyl, amino, phenyl, C$_{2-6}$ alkenyl, C$_{2-6}$ alkynyl, dimethylcarbanoyl, alkoxycarbonyl, trichloromethylthio, alkylsulphonyl or haloalkylsulphonyl or R$^{13}$ and R$^{14}$ together with the nitrogen atom to which they are attached form a heterocyclic ring such as pyrrole; or—N═CR$^{15}$R$^{16}$ where R$^{15}$ is hydrogen or alkylthio and is alkylthio or alkoxy.

Preferably R$^{33}$ is tert-butyl or pentafluoroethyl.

Preferably R$^{34}$ is dialkylamino, for example, dimethylamino or diethylamino.

Examples of compounds of formula (I) wherein R$^1$ is a group of sub-formula (b'):

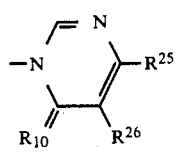

are set out in Table I below.

TABLE I

| COMPOUND NO. | R$^{25}$ | R$^{26}$ | R$^2$ | R$^3$ | R$^4$ | R$^5$ | R$^{10}$ |
|---|---|---|---|---|---|---|---|
| 1 | CF$_3$ | H | H | H | CF$_3$ | H | O |
| 2 | CF$_3$ | H | Cl | H | CF$_3$ | H | O |
| 3 | C$_2$F$_5$ | H | H | H | CF$_3$ | H | O |
| 4 | C$_2$F$_5$ | H | Cl | H | CF$_3$ | H | O |
| 5 | CF$_3$ | H | Br | H | CF$_3$ | H | O |
| 6 | C$_2$F$_5$ | H | Br | H | CF$_3$ | H | O |
| 7 | CF$_3$ | H | NO$_2$ | H | CF$_3$ | H | O |
| 8 | CF$_3$ | Br | Cl | H | CF$_3$ | H | O |
| 9 | $^n$C$_3$F$_7$ | H | Cl | H | CF$_3$ | H | O |
| 10 | CF$_3$ | H | CN | H | CF$_3$ | H | O |
| 11 | C$_2$F$_5$ | H | CN | H | CF$_3$ | H | O |
| 12 | C$_2$F$_5$ | Br | Br | H | CF$_3$ | H | O |
| 13 | CF$_3$ | H | F | H | CF$_3$ | H | O |
| 19 | CF$_3$ | H | Cl | H | CF$_3$ | H | S |
| 21 | C$_2$F$_5$ | H | F | H | CF$_3$ | H | O |
| 22 | C$_2$F$_5$ | H | Cl | H | OCF$_3$ | H | O |

Examples of compounds of formula (I) wherein R$^1$ is a group of sub-formula (a')

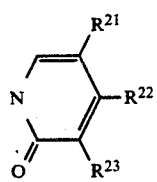

are set out in Table II below.

TABLE II

| COMPOUND NO. | R$^{21}$ | R$^{22}$ | R$^{23}$ | R$^2$ | R$^3$ | R$^4$ | R$^5$ |
|---|---|---|---|---|---|---|---|
| 14 | H | CF$_3$ | H | Cl | H | CF$_3$ | H |
| 15 | CF$_3$ | H | NO$_2$ | Cl | H | CF$_3$ | H |
| 16 | Br | CF$_3$ | H | Cl | H | CF$_3$ | H |
| 17 | CF$_3$ | H | CN | Cl | H | CF$_3$ | H |

TABLE II-continued

| COMPOUND NO. | $R^{21}$ | $R^{22}$ | $R^{23}$ | $R^2$ | $R^3$ | $R^4$ | $R^5$ |
|---|---|---|---|---|---|---|---|
| 18 | $CF_3$ | H | Br | Cl | H | $CF_3$ | H |

Examples of compounds of formula (I) wherein $R^1$ is a group of sub-formula (e')

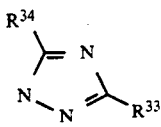
(e')

are set out in Table III below.

TABLE III

| COMPOUND NO. | $R^{33}$ | $R^{34}$ | $R^2$ | $R^3$ | $R^4$ | $R^5$ |
|---|---|---|---|---|---|---|
| 20 | $C(CH_3)_3$ | $N(C_2H_5)_2$ | Cl | H | $CF_3$ | H |

Examples of compounds of formula (I) wherein $R^1$ is a group of sub-formula (c')

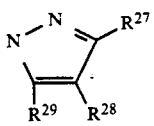
(c')

are set out in Table IV below.

TABLE IV

| COMPOUND NO. | $R^{27}$ | $R^{28}$ | $R^{29}$ | $R^2$ | $R^3$ | $R^4$ | $R^5$ |
|---|---|---|---|---|---|---|---|
| 23 | $N(CH_3)_2$ | $SCF_3$ | H | Cl | H | $CF_3$ | H |

Compounds of formula (I) can be prepared by reacting a compound of formula (II):

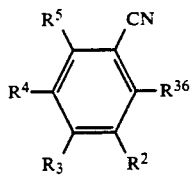
(II)

wherein $R^1$, $R^2$, $R^3$, $R^4$ and $R^5$ are as defined in relation to formula (I) and $R^{36}$ is a leaving group; with a compound of formula (III):

$H-R^1$ (III)

wherein $R^1$ is as defined in relation to formula (I) and thereafter if desired (a) converting a group $R^2-R^5$ to a different such group, and/or (b) converting a substituent on the group $R^1$ to a different substituent. $R^{36}$ is suitably fluorine, chlorine, bromine, trifluoromethylsulphonyloxy or methanesulphonyloxy.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, toluene, an alcohol, an ether, such as tetrahydrofuran, or an aprotic polar solvent such as dimethylformamide or dimethylacetamide.

If necessary an appropriate catalyst such as a crown ether, potassium fluoride or copper can be added depending upon the precise nature of $R^{36}$.

Alternatively, compounds of formula (I) can be prepared by the following process:

(a) preparation of a compound of formula (Ia)

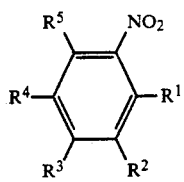
(Ia)

by reacting a compound of formula (IIa)

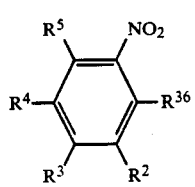
(IIa)

wherein $R^1$, $R^2$, $R^3$, $R^4$, and $R^5$ are as defined in relation to formula (I) and $R^{36}$ is a leaving group as defined above, with a compound of formula (III):

$H-R^1$ (III)

and;

(b) reduction of the nitro group to form a compound of formula (Ib):

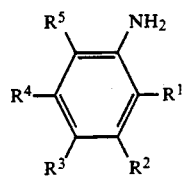
(Ib)

by reacting with a reducing agent, such as stannous chloride, in acid conditions, for example, in a solution in concentrated hydrochloric acid. Moderate temperatures of from 2 to 45° C. are suitably employed. Alternatively, the reduction may be carried out using reduced iron powder in a hydroxylic solvent, such as isopropanol in the presence of an acid catalyst, for example, hydrochloric acid. Moderate temperatures of from 2 to 90° C. are suitably employed; and either (c) subsequent cyanation of the compound of formula (Ib) by, for example, reaction with t-butylnitrite and copper cyanide. This step is suitably carried out in an organic solvent such as acetonitrile at low temperatures of from −20° C. to +20° C. preferably at about 0° C.; or (d) halogenation of the compound of formula (Ib) by, for example, reaction with t-butylnitrite and a copper halide salt such as copper (I) iodide or copper (I) bromide. This step is suitably carried out in an organic solvent such as acetonitrile at low temperatures of from −20° C. to +20° C. preferably at about 0° C. The halide product is then further reacted with copper (I) cyanide in the presence of copper (I) iodide in a dipolar aprotic solvent such as dimethylformamide or N-methyl-pyrolidone at 150-180° C. to give a compound of formula (I).

Conversion of a group $R^2$–$R^5$ to a different such group or converting a substituent on $R^1$ to a different substituent may be carried out by conventional methods. In particular compounds of formula (I) wherein $R^2$, $R^4$, and/or a substituent on $R^1$ is nitro can be converted into the corresponding compound of formula (I) wherein that group is halo by reduction of the nitro group to an amino group to form, for example, a compound of formula (IV):

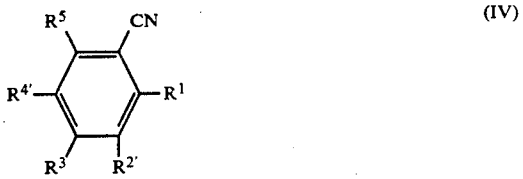                                          (IV)

wherein $R^1$, $R^3$ and $R^5$ are as defined in relation to formula (I) and $R^{2'}$ and $R^{4'}$ are amino or are equivalent to $R^2$ or $R^4$ as defined in relation to formula (I) respectively provided that at least one of $R^{2'}$ or $R^{4'}$ is amino; and thereafter converting the amino group $R^{2'}$, and/or $R^{4'}$ to halo. Certain compounds of formula (IV) are novel and as such form a further aspect of the invention.

Reduction of the nitro group to form a compound of formula (IV) may be carried out as previously described for a compound of formula (IIa).

Subsequent conversion of the amine to halogen may be carried out by reaction with t-butylnitrite and a copper halide salt such as copper (I) iodide. This step is suitably carried out in an organic solvent such as acetonitrile at low temperatures of from $-20°$ C. to $+20°$ C. preferably at about $0°$ C.

Similar reactions can be carried out when the nitro group is a substituent on the group $R^1$.

Compounds of formula (I) where $R^1$ is the sub group (b) and $R^{26}$ is hydrogen may be converted to the corresponding compounds of formula (I) where $R^{26}$ is halogen by conventional methods, for example, bromination with bromine in acetic acid, preferably in the presence of a base such as sodium acetate, or to compounds where $R^{26}$ is nitro by reaction with nitrating agents, such as nitronium tetrafluoroborate, in a polar solvent, such as acetonitile or sulpholane.

Compounds of formula (I) containing a —$SR^6$ group can be converted to the corresponding compounds of formula (I), where containing a —$SOR^6$ or —$SO_2R^6$ group by reaction with an oxidising agent such as m-chloro-perbenzoic acid.

Conversion of compounds of formula (I) or (III) where $R^1$ is sub group (b) where $R^{26}$ is formyl to difluoromethyl, or where $R^{26}$ is 1-hydroxyalkyl to 1-fluoroalkyl can be achieved by reaction with diethylamino sulphur trifluoride.

Compounds of formula (I) where $R^4$ is trifluoromethylthio can be prepared from the corresponding halogen derivatives, preferably where $R^4$ is iodine, by reaction with trifluoromethylthio copper.

Compound of formula (I) wherein $R^1$ is a sub group (a) or (b) and where $R^{10}$ is oxygen can be converted to sulphur by reaction with a thionating agent, such as Lawesson's reagent or $P_2S_5$, suitably at reflux.

Compounds of formula (II) wherein $R^2$ is chlorine, bromine or cyano, $R^3$ is hydrogen, $R^4$ is trifluoromethyl, $R^5$ is hydrogen and $R^{36}$ is fluorine or chlorine are novel and as such form a further aspect of the invention.

The following compounds are also novel and are claimed as particularly useful intermediates in these processes:- 2,6-dicyano-4-trifluoromethylaniline 4-chloro-2,6-dicyano-trifluoromethylbenzene 4-amino-3-chloro-5-cyano-trifluoromethylbenzene 3-chloro-4-fluoro-5-cyano-trifluoromethylbenzene 4-amino-3-bromo-5-cyano-trifluoromethylbenzene 3-bromo-4-chloro-5-cyano-trifluoromethylbenzene 3-bromo-4-fluoro-5-cyano-trifluoromethylbenzene 2-chloro-6-nitro-4-trifluoromethoxyaniline 3,4-dichloro-5-nitro-trifluoromethoxybenzene 3-chloro-4-fluoro-5-nitro-trifluoromethoxybenzene.

Compounds of formula (II) can be prepared by reacting a compound of formula (V):

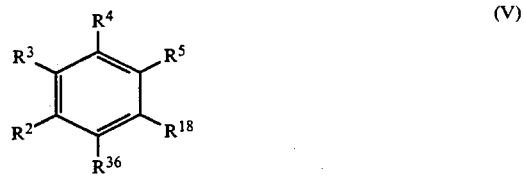                                          (V)

wherein $R^2$, $R^3$, $R^4$, $R^5$ and $R^{36}$ are as hereinbefore defined, and $R^{18}$ is halogen such as bromine, with a cyanide salt such as copper (I) cyanide in an organic solvent. The reaction is suitably carried out in an organic solvent such as quinoline, preferably at elevated temperature of 200 to 250° C. The reaction may optionally be carried out in the presence of a palladium catalyst.

Alternatively $R^{18}$ in formula (V) may be amino, and the reaction then requires the addition of t-butylnitrite in a suitable organic solvent such as acetonitrile. The reaction in this case is suitably effected at low temperatures of from 0° C. to 10° C.

Compounds of formula (V) where $R^{18}$ is halogen are either known compounds or they can be prepared from known compounds by conventional methods.

Compounds of formula (V) where $R^{18}$ is amino are novel and are prepared by reducing the corresponding compound where $R^{18}$ is nitro.

The conversion of groups $R^2$–$R^5$ to different such groups may be carried out on the compound of formula (II) prior to coupling with the compound of formula (III), if desired. This may produce novel intermediates for example where nitro groups $R^2$ and $R^4$ are converted to amino groups prior to halogenation. The methods for a conversion of this type is suitably the same as described above in relation to the equivalent conversions on the compounds of formula (I).

Compounds of formula (II) are either known compounds or they can be prepared from known compounds by conventional methods.

Compounds of formula (III) are either known compounds or they can be prepared from known compounds by conventional methods.

Compounds of formula (III) where $R^1$ is a sub group (b) and where $R^{10}$ is oxygen, $R^{24}$ is hydrogen, $R^{25}$ is haloalkyl: and $R^{26}$ is hydrogen are novel and form a further aspect of the invention.

Suitable reactions for the preparation of compounds of formula (II) are shown in Scheme 1 in which the number given over the reaction arrow relates to the Preparation number under which reaction conditions are detailed.

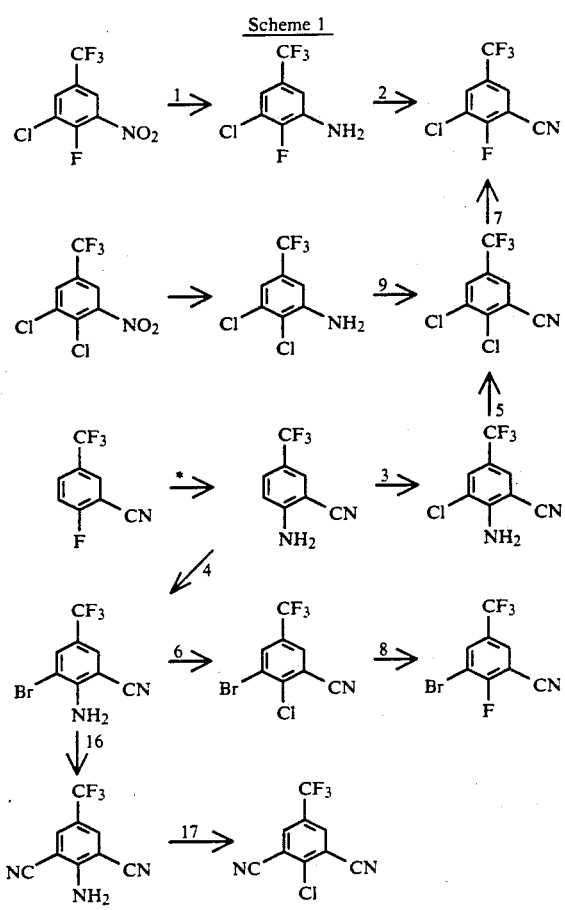

Scheme 1

Compounds of formula (III) can be prepared by general methods known in the art such as (a) condensation of a beta-ketoester of formula (IX):

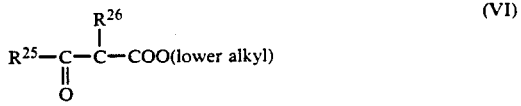

with thiourea or an S-alkyl isothiourea to give a compound of formula (VII):

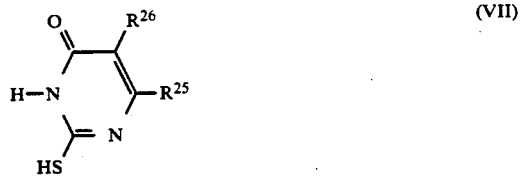

and subsequent desulphurisation with Raney nickel to give a compound of formula (III) where $R^{24}$ is hydrogen; or (b) condensation of the beta-ketoester with formamidine to give the compound of formula (III) where $R^{24}$ is hydrogen; or (c) halogenation of 4-($R^{25}$)-pyrimidin-6-one by conventional methods to give 5-halo-4-($R^{25}$)-pyrimidin-6-one, followed by:

(i) reaction with metal alkoxide eg. sodium, in the appropriate alcohol, such as methanol or ethanol, in pyridine solvent and in the presence of copper (I) iodide, preferably at a temperature from 80–100° C., to give a compound of formula (III) where $R^{26}$ is alkoxy; or (ii) reaction with sodium hydride in a solvent, such as tetrahydrofuran, followed by alkyllithium eg. tertiary-butyllithium, and subsequent reaction with an electrophile, such as dimethylformamide or dialkyldisulphide, to give a compound of formula (III) where $R^{26}$ is formyl or $SR^{6.}$ The compound of formula (III) where $R^{26}$ is formyl can be further reacted with reducing agents, such as sodium borohydride or with Grignard reagents to give compounds of formula (III) where $R^{26}$ is 1-hydroxyalkyl.

Alternatively, compounds of formula (III) when $R^1$ is a group of sub-formula (b) and $R^{24}$ is hydrogen can be prepared by reacting a compound of formula (VIII):

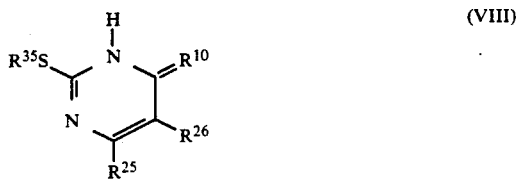

(VIII)

wherein $R^{35}$ is hydrogen or $C_{1-4}$ alkyl such as ethyl with Raney Nickel in an appropriate solvent such as aqueous ammonia.

Compounds of formula (VIII) are either known compounds or they can be prepared from known compounds by known methods (see for example A Giner-Sorolla, A Bendick: J. Am. Chem. Soc., 1958, 80, 5744).

Further details of the processes for preparation of the compounds may be ascertained from the Examples set out hereinafter.

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of solid preparations that may be applied diluted or undiluted.

Solid compositions that may be applied undiluted may be in the form of dusting powders wherein the active ingredient is mixed with a solid diluent or carrier, eg kaolin, bentonite, kieselguhr, silica or talc. Or the solid composition may be in the form of granules wherein the active ingredient is absorbed on a non-porous granular material, for example, calcium carbonate, or may be impregnated in a porous granular material, for example, pumice or gypsum.

Solid compositions that may be applied diluted may be in the form of wettable powders wherein the active ingredient is mixed with a solid diluent or carrier, such as kaolin, kieselguhr or silica and appropriate surface acting agents or they may be in the form of water dispersible granules, wherein the active ingredient is mixed with a solid diluent or carrier, for example, kaolin, kieselguhr or silica and an appropriate surface acting agent, and then granulated.

Alternatively, the compositions may be in the form of liquid preparations to be used as dips, sprays or aerosol dispersions or non-aqueous solutions of the active ingredient and are usually diluted before application.

Aqueous dispersions of the active ingredient which may be applied diluted may be in the form of suspension concentrates wherein the active ingredient is dispersed in an aqueous media. These compositions contain dispersing/ wetting agents and one or more stabilizing agents, for example, bentonite clays and/or polysaccharide gels. Additional further components may be included such as antifreeze agents, for example, ethylene glycol, propylene glycol or salts, and biocides, for example, Proxel GXL (1,2-benzisothiazolin-3-one).

Other aqueous dispersions of the active ingredient may be in the form of microcapsule suspensions wherein the active ingredient is encapsulated, as a high strength water immiscible solution, with a polymer and the subsequent microcapsules are dispersed in aqueous media. The microencapsulation technique used may be of the type described in the patent literature. These compositions contain dispersing/wetting agents and one or more stabilizing agents, for example, bentonite clays and/or polysaccharide gels. Additional further components may be included such as anti-freeze agents and biocides as previously described.

Other aqueous dispersions of the active ingredient may be in the form of oil in water emulsions wherein the active ingredient is dissolved in a suitable solvent, for example, an aromatic hydrocarbon such as trimethylbenzene or a ketonic solvent such as di-hydroisophorone alone with one or more emulsifying agents and then emulsifying the solution so obtained into water which may contain further surface active agents. Other suitable organic solvents are ethylene dichloride, toluene, kerosene, white oil, methylnapthalene, xylenes, trichloroethylene, vegetable oils, N-methyl-2-pyrrolidone and isophorone. Alternatively liquid compositions may be in the form of non-aqueous solutions to be used diluted or undiluted as sprays or aerosol fogs.

Non-aqueous preparations that may be applied undiluted may be in the form of low volume or ultra low volume concentrates wherein the active ingredient is dissolved in a suitable solvent or mixture of solvents, for example, an aromatic hydrocarbon such as trimethylbenzene or aliphatic hydrocarbon such as kerosene. Other suitable solvents are isophorone, di-hydroisophorone, toluene, xylenes, methylnapthalenes, N-methylpyrrolidone, mineral oil and vegetable oils. These preparations are optionally diluted before application with paraffinic solvents, such as diesel oil.

Other non-aqueous preparations may be in the form of emulsifiable concentrates wherein the active ingredient is dissolved in a suitable solvent, for example, trimethylbenzenes or methylcyclohexanone, with one or more emulsifying agents. Other suitable solvents are as previously described. These preparations are diluted in water to form aqueous dispersions before application.

Further formulation types may include preparations for special use such as aerosols wherein the composition will contain the active ingredient or ingredients, a propellant and an inert diluent, for example, odourless kerosenes or alkylated benzenes. In a preferred form, aerosol compositions may contain from 0.005% to 4% of active ingredient or ingredients, the remainder of the composition may be aqueous based in which an aqueous component is dispersed in a solution of active ingredient in a solvent, such as previously described, and a propellant by using one or more surface active agents. Aerosol compositions may optionally incorporate other additives, for example, knockdown agents, synergists, perfumes and corrosion inhibitors.

Other formulations for special purposes may be in the form of ready for use sprays wherein the active ingredient is dissolved in a solvent, for example, odourless kerosenes and alkylated benzenes and applied through a hard pump device to be used as a residual spray. These compositions may optionally incorporate other additives such as knockdown agents, synergists and perfumes.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000g/ha) is particularly useful.

In use the compositions are applied to the pests, to the locus of the pests, to the habitat of the pests, or to growing plants liable to infestation by the pests, by any of the known means of applying pesticidal compositions, The compounds of the invention may be the sole active ingredient of the composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:
a) Pyrethroids such as permethrin, esfenvalerate, deltamethrin, cyhalothrin in particular lambdacyhalothrin, biphenthrin, fenpropathrin, cyfluthrin, tefluthrin, fish safe pyrethroids for example ethofenprox, natural pyrethrin, s-bioallethrin, fenfluthrin, prallethrin, tetramethrin, and 5-benzyl-3-furylmethyl-(E)-(1R,3S)-2,2-dimethyl-3-(2-oxothiolan-3-ylidenemethyl)-cyclopropane carboxylate;
b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphos-methyl, fenitrothion or diazionon;
c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;
d) Benzoyl ureas such as triflumeron, or chlorofluazuron;
e) Organic tin compounds such as cyhexatin, fenbutatin oxide, azocyclotin;
f) Macrolides such as avermectins or milbemyins, for example such as abamectin, avermectin, and milbemycin;
g) Hormones such as pheromones;
h) Organochlorine compounds such as benzene hexachloride, DDT, chlordane or dieldrin;
i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant-growth regulators for inclusion in the compositions will depend upon the intended target and the effect required. An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compounds of formula I and compositions comprising them have shown themselves active against a variety of insect and other invertebrate pests. They are particularly useful in controlling public health pests such as flies and cockroaches. They may also be active against organophosphate and pyrethroid resistant strains of pests such as houseflies (*Musca domestica*). They may be effective in combating both susceptible and resistant strains of the pests in their adult, larval and intermediate stages of growth, and may be applied to the infested host animal by topical, oral or parenteral administration.

The following Preparations and Examples illustrate various aspects of the invention. In the Preparations and Examples the compounds were identified and characterised by means of the melting points, nuclear magnetic resonance spectroscopy (in $CDCl_3$ or $d_6DMSO$, using a Jeol GSX machine at 270 mHz), mass spectroscopy (using a VG TRIO 1 machine) or infra red spectroscopy (using a Perkin-Elmer Model 881). The Preparations 1–9 and 16–17 are also illustrated schematically in Scheme 1.

PREPARATION 1

This description illustrates the preparation of 3-amino-5-chloro-4-fluoro-trifluoromethylbenzene.

5-Chloro-4-fluoro-3-nitro-trifluoromethylbenzene (50g) was added to a cooled (5° C.) solution of stannous chloride (140g) in concentrated aqueous hydrochloric acid (187ml). After stirring for several hours at the ambient temperature (about 22° C.), the reaction mixture was stood overnight. After basification by the addition of sodium hydroxide, the reaction mixture was extracted with ethyl acetate. The organic layer was washed with water, dried, and the solvent removed by evaporation under reduced pressure. The residual yellow oil was kugelrohr distilled under reduced pressure to give 3-amino-5-chloro-4-fluoro-trifluoromethylbenzene (32g): boiling point 105° C./11 mm Hg;

$^1H$ NMR $\delta(CDCl_3)$ 7.03 (1H, dq), 6.90 (1H, dq), 4.05 (2H, broad s).

PREPARATION 2

This description illustrates the preparation of 3-chloro-4-fluoro-5-cyano-trifluoromethylbenzene.

A solution of 3-amino-5-chloro-4-fluorotrifluoromethylbenzene (3g) in acetonitrile (10ml) was added dropwise to a stirred suspension of copper (I) cyanide (1.26g) in dry acetonitrile (50ml) whilst the reaction temperature was maintained at 0° C. After the addition was complete, the reaction mixture was allowed to warm to the ambient temperature (about 23°

C.) and left overnight. The reaction mixture was poured into water, extracted with diethyl ether, dried over anhydrous magnesium sulphate and filtered. Evaporation of the solvent, under reduced pressure, gave a brown oil, which was flushed through a plug of silica gel using petroleum ether (boiling range 60–80° C.) containing diethyl ether (20% by volume) as eluent. After removal of the solvent, under reduced pressure, kugelrohr distillation of the residue gave two fractions, the first of which (boiling point 110° C. at 15mmHg) was predominantly composed of 3-chloro-4-fluoro-5-cyano-trifluoromethylbenzene. This material was used without further purification.

$^1$H NMR $\delta$(CDCl$_3$) 7.95 (1H, m); 7.85 (1H, m).

PREPARATION 3

This description illustrates the preparation of 4-amino-3-chloro-5-cyano-trifluoromethylbenzene.

Chlorine gas was passed through a stirred solution of 4-amino-3-cyano-trifluoromethylbenzene (5g) in carbon tetachloride (75ml) until the absence of starting material was confirmed by gas liquid chromatography. Flow of the gas was then stopped and evaporation of the solvent under reduced pressure gave 4-amino-3-chloro-5-cyanotrifluoromethylbenzene as an orange solid (5.5g).

$^1$H NMR $\delta$(CDCl$_3$/d$_6$-DMSO): 7.67 (1H, d); 7.55 (1H,d); 5.85 (2H, broad s).

PREPARATION 4

This description illustrates the preparation of 4-amino-3-bromo-5-cyanotrifluoromethylbenzene.

Bromine (a total of 4.9g) was added in two portions to a stirred suspension of 4-amino-3-cyano-benzotrifluoride (3g) and sodium acetate trihydrate (1g) in carbon tetrachloride (65ml). The mixture was heated to 80° C. until the absence of starting material was confirmed by gas liquid chromatography. Evaporation of the solvent under reduced pressure gave a pale green solid, which was dissolved in ethyl acetate, and washed with water and brine. After drying over anhydrous magnesium sulphate, the solvent was removed to give 4-amino-3-bromo-5-cyano-trifluoromethylbenzene (3.63g) as an oil which solidified on standing.

$^1$H NMR $\delta$(CDCl$_3$)7.85 (1H,d); 7.65 (b 1H,s); 5.25 (2H, broad s).

PREPARATION 5

This description illustrates the preparation of 3-cyano-4,5-dichloro-trifluoromethylbenzene.

4-Amino-3-chloro-5-cyano-trifluoromethylbenzene (5.1g) (Preparation 3) in dry acetonitrile (0.25 ml) was added dropwise to a stirred suspension of copper (II) chloride (3.72g) and tertiary butyl nitrite (12.24g) in dry acetonitrile (75 ml) whilst the temperature was maintained between 0 and +5° C. After the addition was complete stirring was continued for a further 2 hours, whereupon the reaction mixture was diluted with dilute aqueous hydrochloric acid, and extracted with ethyl acetate. The organic layer was washed with water, and after drying over anhydrous magnesium sulphate, evaporation of the solvent under reduced pressure gave an orange oil which crystallised on standing. Kugelrohr distillation gave 3-cyano-4,5-dichloro-trifluoromethylbenzene as a pale yellow oil which crystallised on standing.

$^1$H NMR $\delta$(CDCl$_3$): 7.95 (1H,d); 7.85 (1H,d).

PREPARATION 6

4-Amino-3-bromo-5-cyano-trifluoromethylbenzene (Preparation 4) was converted into 3-bromo-4-chloro-5-cyano-trifluoromethylbenzene using the general method of Preparation 5.

$^1$H NMR $\delta$(CDCl$_3$) 8.12 (1H,d); 7.90 (1H,d).

PREPARATION 7

This description illustrates an alternate preparation of 3-chloro-4-fluoro-5-cyano-trifluoromethylbenzene.

Dry potassium fluoride (1.94g) was added to a flask containing dry toluene (31 ml), dry dimethylformamide (7.8ml) and a catalytic amount of 18-crown-6. The stirred mixture was heated to reflux, and approximately 25 mls of the distillate was collected. After cooling to ambient temperature, 3-cyano-4,5-dichloro-trifluoromethylbenzene (4g) was added in one portion, and the stirred mixture was heated to 130° C. for 16 hours, and then to 145° C. for 24 hours. After cooling to ambient temperature, the reaction mixture was filtered, the residue washed with ethyl acetate, and the combined filtrate washed with brine. After drying over anhydrous magnesium sulphate, evaporation under reduced pressure gave a brown oil which was subjected to kugelrohr distillation, to give 3-chloro-4-fluoro-5-cyano-trifluoromethylbenzene as a pale yellow liquid (3.17g).

$^1$H NMR $\delta$(CDCl$_3$) 7.95 (1H,dq); 7.85 (1H,dq)

PREPARATION 8

3-Bromo-4-fluoro-5-cyano-trifluoromethylbenzene was prepared from 3-bromo-4-chloro-5-cyano-trifluoromethylbenzene (Preparation 6) using the general method of Preparation 7.

$^1$H NMR $\delta$(CDCl$_3$) 8.10 (1H,dq); 7.89 (1H,dq).

PREPARATION 9

This description illustrates an alternative procedure from that described in Preparation 5 for the preparation of 3-cyano-4,5-dichloro-trifluoromethylbenzene.

Sodium nitrite (2.3g) was added in portions to concentrated sulphuric acid (18.0g) at room temperature. 3-Amino-4,5-dichloro-trifluoromethylbenzene (6.9g) was added portionwise, during the course of which time acetic acid (15ml) was added to the stirred slurry. This slurry was then added dropwise to a cooled (9–10° C.) solution of sodium cyanide (5.9), copper (I) cyanide (5.4g), and sodium acetate trihydrate (60g) in water (60ml).

After the addition was complete, the mixture was stirred and allowed to warm to ambient temperature over the course of one hour, and then stirred for a further hour. The pH of the reaction mixture was adjusted to 8.5 using aqueous sodium hydroxide solution and the mixture was then extracted with ethyl acetate. The organic layer was washed with water and brine and dried over anhydrous magnesium sulphate. Evaporation of the solvent under reduced pressure and distillation gave 3-cyano-4,5-dichloro-trifluoromethylbenzene characterised by an NMR spectrum which was identical to that given in preparation 5.

PREPARATION 10

This description illustrates the preparation of 4-pentafluoroethyl-2-thiouracil.

Thiourea (3g) was added to a solution of sodium methoxide in methanol (previously prepared by adding sodium metal (1.089g) to dry methanol (20ml)). This was followed by ethyl pentafluoropropionyl acetate (9.61g) and the reaction mixture was heated under reflux for 3 days. After cooling the solvent was evaporated, under reduced pressure, to give a brown solid, which was then acidified with dilute aqueous hydrochloric acid and extracted with diethyl ether. The combined organic extracts were dried, and removal of the solvent by evaporation, under reduced pressure, gave 4-pentafluoroethyl-2-thiouracil (4.14g), which was carried to Preparation 11.

$^1$H NMR $\delta$(CDCl$_3$) 12.30 (1H, broad s); 11.65 (1H,broad s); 6.20 (1H,s).

PREPARATION 11

This description illustrates the preparation of 4-pentafluoroethylpyrimidin-6-one.

Raney Nickel (0.83g, of a 50% dispersion in water) was added to a suspension of 4-pentafluoroethyl-2-thiouracil (0.5g) (Preparation 10) in a mixture of concentrated aqueous ammonia (0.23ml) in water (6ml). The reaction mixture was heated to reflux for 5.5 hours, cooled, stood overnight, and filtered hot through celite. The filtrate was concentrated by evaporation of the solvent under reduced pressure to give the desired compound as a pale green solid. Sublimation gave 4-pentafluoroethylpyrimidin-6-one as a white solid of melting point 122–126° C.

$^1$H NMR $\delta$(CDCl$_3$)/d$_6$ DMSO: 8.13 (s); 6.81 (s).

PREPARATION 12

This description illustrates the preparation of 1-(2-amino-6-fluoro-4-trifluoromethylphenyl)-4-trifluoromethylpyrimidin-6-one.

Reduced iron powder (0.18g) was added to a suspension of 1-(2-fluoro-6-nitro-4-trifluoromethylphenyl)-4-trifluoromethylpyrimidin-6-one (0.6g) in a mixture of isopropanol (6ml) and water (0.6ml). Concentrated hydrochloric acid (1 drop) was added, and the reaction mixture was heated to 100° C. for a period of 5 hours. After cooling to ambient temperature, the reaction mixture was filtered through celite, and the residue washed with ethyl acetate. Evaporation of the filtrate under reduced pressure gave 1-(2-amino-6-fluoro-4-trifluoromethylphenyl)-4-trifluoromethylpyrimidin-6-one as an off-white solid, which was used in Preparation 13 without further purification.

$^1$H NMR $\delta$(CDCl$_3$+d$_6$ DMSO): 8.1 (1H,s); 7.98 (2H,s); 6.78 (1H,dd); 5.10 (2H,broad s).

PREPARATION 13

1-(2-Bromo-6-fluoro-4-trifluoromethylphenyl)-4-trifluoromethylpyrimidin-6-one was prepared from 1-(2-amino-6-fluoro-4-trifluoromethylphenyl)-4-trifluoromethylpyrimidin-6-one (the product of preparation 12) according to the method given in preparation 5. In this preparation, copper (II) bromide was the halide used, and the product was purified by column chromatography on silica gel using petroleum ether (boiling range 60–80° C.) containing ethyl acetate (20% by volume) as eluent.

$^1$H NMR $\delta$(CDCl$_3$): 8.07 (1H,s); 7.88 (1H,s); 7.88 (1H,dd); 7.00 (1H,s).

PREPARATION 14

4-n-Heptafluoropropyl-2-thiouracil was prepared from thiourea and ethyl heptafluorobutylacetate according to the procedure given in preparation 10.

Melting point: 216–217° C.
$^1$H NMR $\delta$(d$^6$DMSO): 12.83 (1H,broad s); 6.35 (1H,broad s); 3.35 (1H,broad s).

PREPARATION 15 from 4-n-heptafluoropropyl-2-thiouracil and Raney Nickel according the procedure given in Preparation 11.

$^1$H NMR $\delta$(CDCl$_3$/d$^6$-DMSO): 8.14 (1H,s); 6.78 (1H,s),

PREPARATION 16

This description illustrates the preparation of 2,6-dicyano-4-trifluoromethyl-aniline.

A stirred suspension of copper (I) cyanide (3g) and 4-amino-3-bromo-5-cyano-trifluoromethylbenzene (from Preparation 4) (6g) in dry, distilled N-methyl pyrollidinone (50ml) was heated to 170° C. for 16 hours. After cooling to ambient temperature, the reaction mixture was poured into water and ammonium hydroxide, filtered, and the filtrate extracted with diethyl ether. The organic layer was dried over anhydrous magnesium sulphate and the solvent evaporated under reduced pressure, to give a yellow oil. Chromatography on silica gel using petroleum ether (boiling range 60–80° C.) containing ethyl acetate (16% by volume) gave 2,6-dicyano-4-trifluoromethyl aniline as a pale yellow solid.

$^1$H NMR $\delta$(CDCl$_3$) 7.86 (2H,s); 5.50 (2H,broad s).

PREPARATION 17

4-Chloro-3,5-dicyano-trifluoromethylbenzene was prepared from 2,6-dicyano-4-trifluoromethylaniline according to the method given in Preparation 5.

$^1$H NMR $\delta$(CDCl$_3$) 8.15 (s)

PREPARATION 18

This description illustrates the preparation of 3-cyano-5-trifluoromethyl-2-pyridone.

A solution of 3-formyl-5-trifluoromethyl-2-pyridone (3.5g) (UK Application No. 89310162.6), hydroxylamine hydrochloride (1.42g) and sodium formate (1.39g) in 98% formic acid (42ml) was heated to reflux for a period of 20 hours. After cooling to ambient temperature, the reaction mixture was poured into water, and rigorously extracted with ethyl acetate. The combined organic extracts were washed with saturated aqueous sodium bicarbonate solution, followed by brine, and dried over anhydrous magnesium sulphate. Removal of the solvent under reduced pressure gave 3-cyano-5-trifluoromethyl-2-pyridone as an off-white solid which was used without further purification.

$^1$H NMR $\delta$(d$^6$DMSO): 8.54 (1H,d); 8.30 (1H,d).

The compound was later shown to contain some residual 3-bromo-5-trifluoromethyl-2-pyridone, which was carried through into Example 2M.

PREPARATION 19

This description illustrates the preparation of 1-(2-fluoro-6-nitro-4-trifluoromethylphenyl)-4-pentafluoro-ethylpyrimidin-6-one.

A dry reaction flask was purged with nitrogen and charged with a 50% suspension of sodium hydride (0.123g). The sodium hydride was suspended in DMF (10ml). Solid 6-pentafluoromethylpyrimidin-6-one was added in portions. The mixture was stirred for a further 30 minutes and then 3,4-difluoro-5-nitro-benzotrifluoride (0.58g) was added in one portion. The reaction mixture was vigorously stirred for 30 minutes and then poured into water and extracted with diethyl ether. The combined organic layers were washed with water and brine, and dried over magnesium sulphate. The solvent was removed under reduced pressure to afford a yellow residue. The residue was purified using silica gel and a 1:1 mixture of ethyl acetate and petroleum ether (boiling range 60-80° C.) to give the desired compound.

melting point: 135.5–137° C.

$^1$H NMR $\delta$(CDCl$_3$): 8.38 (1H,s); 8.30 (1H,s); 7.98 (1H,dd); 7.01 (1H,s).

PREPARATION 20

1-(2-Amino-6-fluoro-4-trifluoromethylphenyl)-4-pentafluoroethylpyrimidin-6-one was prepared from 1-(2-fluoro-6-nitro-4-trifluoromethylphenyl)-4-pentafluoroethyl pyrimidin-6-one (the product of Preparation 19) according to the method given in Preparation 12.

$^1$H NMR $\delta$(CDCl$_3$): 8.10 (1H,s); 7.05 (1H,s); 6.95 (1H,s); 6.93 (1H,d); 4.15 (2H,broad s).

PREPARATION 21

1-(2-Bromo-6-fluoro-4-trifluoromethylphenyl)-4-pentafluoroethylpyrimidin-6-one was prepared from 1-(2-amino-6-fluoro-4-trifluoromethylphenyl)-4-pentafluoroethylpyrimidin-6-one (the product of Preparation 20) according to the method given in Preparation 5. In this preparation, copper (II) bromide was the halide used.

melting point: 115-117.5° C.

$^1$H NMR $\delta$(CDCl$_3$): 8.07 (1H,s); 7.90 (1H,s); 7.6 (1H,dd); 7.05 (1H,s)

PREPARATION 22

This description illustrates the preparation of 2-chloro-6-nitro-4-trifluoromethoxy-aniline.

Chlorine gas was passed through a solution of 2-nitro-4-trifluoromethoxy-aniline (14.5g) in carbon tetrachloride (175ml). The stirred mixture became solid, and more carbon tetrachloride (50ml) was added. Chlorine gas was passed through the reaction mixture until thin layer chromatography on silica gel, using petroleum ether (boiling range 60-80° C.) containing ethyl acetate (30% by volume) as eluent, demonstrated the absence of starting material. Evaporation of the solvent under reduced pressure gave a dark orange solid, which on trituration with petroleum ether (boiling range 60-80° C.) gave 2-chloro-4-trifluoromethoxy-6-nitroaniline as an orange solid.

$^1$H NMR $\delta$(CDCl$_3$): 8.04 (1H,d); 7.49 (1H,d); 6.60 (2H, broad s).

PREPARATION 23

3,4-Dichloro-5-nitro-trifluoromethyoxybenzene was prepared from 2-chloro-6-nitro-4-trifluoromethoxyaniline according to the method given in Preparation 5.

$^1$H NMR $\delta$(CDCl$_3$) 7.60 (fine d)

PREPARATION 24

1-(2-Chloro-6-nitro-4-trifluoromethoxyphenyl)-4-pentafluoroethylpyrimidin-6-one was prepared from 3,4-dichloro-5-nitro-trifluoromethoxybenzene and 4-pentafluoroethylpyrimidin-6-one according to the method given in Preparation 19. In this preparation the reaction mixture was heated to 90° C. for 16 hours and the product purified on a Gilson medium performance liquid chromatograph using silica gel and eluting with hexane containing ethyl acetate (5% by volume).

melting point: 139-140.5° C.

$^1$H NMR $\delta$(CDCl$_3$) 8.10 (1H,s); 8.05 (1H,d); 7.80 (1H,d); 7.0 (1H,s).

PREPARATION 25

1-(2-Amino-6-chloro-4-trifluoromethoxyphenyl)-6-pentafluoroethylpyrimidin-6-one was prepared from 1-(2-chloro-6-nitro-4-trifluoromethoxyphenyl)-6-pentafluoroethylpyrimidin-6-one (the product of Preparation 24) according to the method given in preparation 12.

$^1$H NMR $\delta$(CDCl$_3$) 8.02 (1H,s); 7.02 (1H,s); 6.79 (1H,d); 6.69 (1H,d); 4.6 (2H,broad s).

PREPARATION 26

1-(2-Bromo-6-chloro-4-trifluoromethoxyphenyl)-4-pentafluoroethylpyrimidin-6-one was prepared from 1-(2-amino-6-chloro-4-trifluoromethoxyphenyl)-4-pentafluoroethylpyrimidin-6-one (the product of Preparation 25) according to the method given in Preparation 5. In this preparation copper (II) bromide was the halide used.

$^1$H NMR $\delta$(CDCl$_3$) 8.00 (1H,s); 7.60 (1H,d); 7.50 (1H,d); 7.05 (1H,s)

PREPARATION 27

This description illustrates the preparation of 3,4-difluoro-5-nitro-benzotrifluoride.

A mixture of dry potassium fluoride (50g), dry toluene (200ml), dry pyridine (17g) and dry dimethylformamide (17g) was vigorously stirred and heated to reflux temperature. The distillate (50ml) was collected and the refluxing mixture was cooled to 80° C. 4-Chloro-3,5-dinitro-benzotrifluoride (50g) was added to the mixture in portions over 30 minutes. The reaction mixture was then heated at 100° C. under a slow flow of dry nitrogen for 6 hours. After cooling to ambient temperature, the reaction mixture was poured into aqueous sodium bicarbonate solution, and extracted with diethyl ether. The combined organic layers were washed sequentially with aqueous sodium bicarbonate solution (twice), water and brine. After drying, the solution was concentrated by distillation of the diethyl ether and some toluene at atmospheric pressure. As the head temperature reached 110° C. a precipitate formed. The residue was cooled to room temperature, diluted with diethyl ether and filtered through celite. The filtrate was washed with brine. The solvent was removed by distillation at atmospheric pressure. When toluene had ceased to be distilled off, the distillation was continued at reduced pressure. The fraction boiling at 80-90° C. (at 100mg Hg) was predominently composed of 3,4-difluoro-5-nitrobenzotrifluoride.

$^1$H NMR $\delta$(CDCl$_3$): 8.18 (1H,m); 7.78 (1H,m)

EXAMPLE 1

This Example illustrates the preparation of 1-(2-cyano-4-trifluoromethylphenyl)-4-trifluoromethylpyrimidin-6-one (Compound No. 1 in Table I).

A dry reaction flask was purged with nitrogen and charged with 50% sodium hydride (0.16g). The solution hydride was washed with petroleum ether (boiling range: 60-80° C.) and suspended in dry dimethylformamide (DMF, 10 ml).

4-Trifluoromethylpyridimin-6-one (0.5g) was added portionwise, and when the addition was complete the reaction was stirred for a further 30 minutes. 3-Cyano-4-fluoro-trifluoromethylbenzene (1.13g) was added, and the reaction mixture was heated to 90° C. for 16 hours. The reaction mixture was allowed to cool, poured into water, and extracted with ethyl acetate. The organic layer was washed with brine, dried over anhydrous magnesium sulphate and evaporated under reduced pressure to give a brown oil which solidified. The solid was flushed through a plug of silica using petroleum ether (boiling range 60-80° C.) containing diethyl ether (20% by volume) as eluent. Evaporation of the solvent, under reduced pressure, gave a pale brown solid which was triturated with petroleum ether (boiling range 60-80° C.) to give an off-white solid, which was then recrystallised from petroleum ether (boiling range: 60-80° C.) containing diethylether (33% by volume). 1(2-Cyano-4-trifluoromethylphenyl)-4-trifluoromethyl-pyrimidin-6-one was isolated as white needles of melting point : 173-175° C.

$^1$H NMR $\delta$(CDCl$_3$) : 8.22 (1H,s); 8.18 (1H,s); 8.11 (1H, d); 7.7 (1H,d); 7.03 (1H,s).

EXAMPLE 2

The following Examples were prepared according to the general method of Example 1 from appropriate compounds of formula (II) and formula (III):

(a) 1-(2-Chloro-6-cyano-4-trifluoromethylphenyl)-4-trifluoromethylpyridimin-6-one (Compound No. 2 in Table I) was prepared by reaction of the product of preparation 2 and 4-trifluoromethylpyrimidin-6-one:
$^1$H NMR $\delta$(CDCl$_3$) : 8.16 (1H,s); 8.09 (1H,s); 8.07 (1H,s); 7.05 (1H,s)

(b) 1-(2-Cyano-4-trifluoromethylphenyl)-4-pentafluroethylpyrimdin-6-one (compound No 3 in Table I) was prepared by the reaction of 3-cyano-4-fluoro-trifluoromethylbenzene and 4-pentafluoroethylpyrimidin-6-one. The latter compound is available as described in preparation 11.
$^1$H NMR $\delta$(CDCl$_3$/d$_6$-DMSO): 8.39 (1H,s); 8.19 (1H,s); 8.15 (1H,d); 7.80 (1H,d); 7.05 (1H,s)
Melting point (petroleum ether/ethyl acetate, 3:1): 180°5-182° C.

(c) 1-(2-Chloro-6-cyano-4-trifluoromethylphenyl)-4-pentafluoroethylpyrimidin-6-one (compound No 4 in Table I) was prepared by the reaction of 3-chloro-4-fluoro-5-cyano-trifluoromethylbenzene and 4-pentafluoroethylpyrimidin-6-one.
$^1$H NMR $\delta$(CDCl$_3$/d$_6$-DMS0): 8.15 (1H,s); 8.09 (2H,m); 7.09 (1H,s).
Melting point (petroleum ether/ethyl acetate, 5:1): 157.5-159° C.

(d) 1-(2-Bromo-6-cyano-4-trifluoromethylphenyl)-4-trifluoromethylpyrimidin-6-one (compound No 5 in Table I) was prepared by the reaction of 3-bromo-4-fluoro-5-cyano-trifluoromethylbenzene and 4-trifluoromethylpyrimidin-6-one.
$^1$H NMR $\delta$(CDCl$_3$): 8.30 (1H,d); 8.10 (1H,d); 8.08 (1H,s); 7.03 (1H,s).
Melting point (petroleum ether/ethyl acetate, 5:1): 65.5-167° C.

(e) 1-(2-Bromo-6-cyano-4-trifluoromethylphenyl)-4-pentafluoroethylpyrimidin-6-one (compound No 6 in Table I) was prepared by the reaction of 3-bromo-4-fluoro-5-cyanotrifluoromethylbenzene and 4-pentafluoroethylpyrimidin-6-one.
$^1$H NMR $\delta$(CDCl$_3$): 8.30 (1H,d); 8.10 (1H,d); 8.05 (1H,s); 7.09 (1H,s).
Melting point: 147.5-148.5° C.

(f) 1-(2-Cyano-6-nitro-4-trifluoromethylphenyl)-4-trifluoromethylpyrimidin-6-one (Compound No 7 in Table I) was prepared by the reaction of 4-chloro-3-cyano-5-nitrotrifluoromethylbenzene and 4-trifluoromethylpyrimidin-6-one. The former compound is available as described for example in Example 19 (c) of European Patent No. 023100
$^1$H NMR $\delta$(CDCl$_3$): 8.75 (1H,d); 8.49 (1H,s); 8.48 (1H,d); 7.00 (1H,s).

(g) 1-(2-Chloro-6-cyano-4-trifluoromethylphenyl)-4-trifluoromethyl-2-pyridone (Compound No 14 of Table II) was prepared by reacting 3-chloro-4-fluoro-5-cyanotrifluoromethylbenzene and 4-trifluoromethyl-2-pyridone.
$^1$H NMR $\delta$(CDCl$_3$) 8.10 (1H,d); 8.0 (1H,d); 7.26 (1H,dd); 7.04 (1H,s); 6.55 (1H,dd).
Melting point (petroleum ether/ethyl acetate) 139.5-141.4° C.

(h) 1-(2-Chloro-6-cyano-4-trifluoromethylphenyl)-3-nitro-5-trifluoromethyl-2-pyridone (Compound No 15 in Table II) was prepared by the reaction of 3-chloro-4-fluoro-5-cyanotrifluoromethylbenzene and 3-nitro-5-trifluoromethyl-2-pyridone.
$^1$H NMR $\delta$(CDCl$_3$): 8.65 (1H,d); 8.17 (1H,s); 8.08 (1H,d); 7.89 (1H,m).
Melting point (petroleum ether/ethyl acetate): 186.5-187.5° C.

(i) 1-(2-Chloro-6-cyano-4-trifluoromethylphenyl)-5-bromo-4-trifluoromethyl-2-pyridone (Compound No 16 in Table II) was prepared by the reaction of 3-chloro-4-fluoro-5-cyanotrifluoromethylbenzene and 5-bromo-4-trifluoromethyl-2-pyridone.
$^1$H NMR $\delta$(CDCl$_3$) 8.10 (1H,d); 8.01 (1H,d); 7.45 (1H,s); 7.13 (1H,s).
Melting point (petroleum ether/ethyl acetate): 176-177° C.

(j) 1-(2-Chloro-6-cyano-4-trifluoromethylphenyl)-4-n-heptafluoropropyl pyrimidin-6-one (compound No 9 in Table 1) was prepared by the reaction of 3-chloro-4-fluoro-5-cyanotrifluoromethylbenzene and 4-n-heptafluoropropylpyrimidin-6-one.
$^1$H NMR $\delta$(CDCl$_3$) 8.15 (1H,d); 8.08 (1H,d); 8.08 (1H,s); 7.07(1H,s).

(k) 1-(2,6-Dicyano-4-trifluoromethylphenyl)-4-trifluoromethylpyrimidin-6-one (compound no 10 in Table I) was prepared by the reaction of 4-chloro-3,5-dicyanotrifluoromethylbenzene and 4-trifluoropyrimidin-6-one.
Melting Point : 230.4-231.5° C.
$^1$H NMR $\delta$(CDCl$_3$): 8.38 (2H,s); 8.18 (1H,s); 7.08 (1H,s).

(l) 1-(2,6-Dicyano-4-trifluoromethylphenyl)-4-pentafluoroethylpyrimidin-6-one (compound no 11 in Table I) was prepared by the reaction of 4-chloro-3,5-dicyanotrifluoromethylbenzene and 4-pentafluoroethylpyrimidin-6-one.
$^1$H NMR $\delta$(CDCl$_3$) 8.37 (2H,s); 8.17 (1H,s); 7.12 (1H,s).

(m) 1-(2-Chloro-6-cyano-4-trifluoromethylphenyl)-3-cyano-5-trifluoromethyl-2-pyridone (Compound No 17 in Table II) was prepared by the reaction of 3-chloro-4-fluoro-5-cyano-trifluoromethylbenzene and 3-cyano-5-trifluoromethyl-2-pyridone.
$^1$H NMR $\delta$(CDCl$_{13}$): 8.15 (2H,d); 8.05 (1H,d); 7.78 (1H,d)
Further investigation of the reaction mixture indicated the presence of a second compound-1-(2-chloro-6-cyano-4-trifluoromethylphenyl)-3-bromo-5-trifluoromethyl-2-pyridone (Compound No 18 in Table II). This material was formed from 3-bromo-5-trifluoromethyl-2-pyridone present as a contaminant in the 3-cyano-5-trifluoromethyl-2-pyridone. The compound was isolated by medium pressure liquid chromatography using silica gel as the stationary phase and hexane containing diethyl ether (30% by volume) as eluent.

$^1$H NMR δ(CDCl$_3$) 8.11 (1H,d); 8.04 (1H,d); 8.04 (1H,d); 7.56 (1H,d).

EXAMPLE 3

This Example illustrates the preparation of 1-(2-chloro-6-cyano-4-trifluoromethylphenyl)-5-bromo-4-trifluoromethylpyrimidin-6-one (Compound No. 8 in Table I).

Bromine (35mg) was added to a stirred solution of 1-(2-chloro-6-cyano-4-trifluoromethylphenyl)-4-trifluoromethylpyrimidin-6-one (70mg) and sodium acetate trihydrate (77mg) in acetic acid (3.5ml). After stirring for 6 hours, the reaction mixture was allowed to stand overnight, whereupon the solvent was evaporated under reduced pressure. The residual solid was dissolved in ethyl acetate and washed with water, followed by aqueous sodium bicarbonate solution and finally brine. After drying over anhydrous magnesium sulphate the solvent was evaporated under reduced pressure to give 1-(2-chloro-6-cyano-4-trifluoromethylphenyl)-3-bromo-4-trifluoromethylpyrimidin-6-one as a colourless solid.

melting point: 166-167.2° C.

$^1$H NMR δ(CDCl$_3$); 8.17 (1H,d); 8.07 (b 1H,d); 8.00 (1H,s).

EXAMPLE 4

1-(2-Bromo-6-cyano-4-trifluoromethylphenyl-5-bromo-4-pentafluoroethylpyrimidin-6-one (Compound No. 12 in Table I) was prepared from 1-(2-bromo-6-cyano-4-trifluoromethylphenyl)-4-pentafluoroethylpyrimidin-6-one (Compound No. 6 in Table I) and bromine following the procedure given in Preparation 3.

melting point: 155.5-156.5° C.

$^1$H NMR δ(CDCl$_3$): 8.30 (1H,d); 8.11 (1H,d); 8.00 (1H,s).

EXAMPLE 5

This Example illustrates the preparation of 1-(2-chloro-6-cyano-4-trifluoromethylphenyl)-4-trifluoromethylpyrimidin-6-thione (Compound No. 19 in Table I).

Lawesson's Reagent (2,4-bis-(4-methoxyphenyl-1,3-dithia-2,4-diphosphetane-2,4-disulphide) (0.58g) was added to a stirred solution of 1-(b 2-chloro-6-cyano-4-trifluoromethylphenyl)-4-trifluoromethylpyrimidin-6-one (0.3g) in dry, distilled pyridine (1ml). The reaction mixture was heated to 130° C. for 16 hours, followed by further heating to 140° C. for 8 hours. After cooling to ambient temperature, the reaction mixture was dissolved in ethyl acetate, and washed with brine. After drying over anhydrous magnesium sulphate, evaporation of the solvent, under reduced pressure, gave a brown oil. This material was subjected to medium pressure liquid chromatography, on a Gilson apparatus, using silica gel as the stationary phase, eluting first with hexane containing ethyl acetate (5% by volume) and then with hexane containing ethyl acetate (2% by volume). The appropriate fractions were collected to give 1-(2-chloro-6-cyano-4-trifluoromethylphenyl)-4-trifluoromethylpyrimidin-6-thione as an orange solid.

$^1$H NMR δ(CDCl$_3$): 8.15 (1H,s); 8.05 (2H,s); 7.75 (1H,s)

EXAMPLE 6

This Example illustrates the preparation of 1-(2-cyano-6-fluoro-4-trifluoromethylphenyl)-4-trifluoromethylpyrimidin-6-one (Compound No. 13 in Table I).

A mixture of 1-(2-bromo-6-fluoro-4-trifluoromethylphenyl-4-trifluoromethylpyrimidin-6-one (from Preparation 13) (0.15g), copper (I) cyanide (36mg) and copper (I) iodide (76mg) in dry N-methylpyrrolidinone (2ml) was heated to 160° C. for 16 hours. On cooling to ambient temperature the reaction mixture was poured into water and extracted with ethyl acetate. The organic extracts were washed with water and brine, and dried over anhydrous magnesium sulphate. Evaporation of the solvent under reduced pressure gave a brown oil which was then subjected to Kugelrohr distillation under reduced pressure (120° C., 15 mmHg approx) to remove residual N-methylpyrrolidinone. The residue was subjected to medium pressure liquid chromatography on a Gilson apparatus using silica gel as the stationary phase and eluting with hexane containing ethyl acetate (5% by volume). The appropriate fractions were collected to give 1-(2-cyano-6-fluoro-4-trifluoromethylphenyl)-4-trifluoromethylpyrimidin-6-one as a pale yellow solid.

Melting point: 164-166.5° C.

$^1$H NMR δ(CDCl$_3$): 8.28 (1H,s); 7.98 (1H,s); 7.90 (1H,dd); 7.02 (1H,s)

EXAMPLE 7

This Example illustrates the preparation of 1-(2-chloro-6-cyano-4-trifluoromethylphenyl)-3-tertiary-butyl-5-diethylamino-1,2,4-triazole (Compound No. 20 in Table III).

Step (a)

1-(2-Chloro-6-nitro-4-trifluoromethylphenyl)-3-tertiary-butyl-5-diethylamino-1,2,4-triazole (0.6g) was dissolved in methanol (20ml) and the solution warmed to 50° C. A solution of stannous chloride dihydrate (2.3g) in concentrated hydrochloric acid (20ml) was added with vigorous stirring. The reaction mixture was allowed to cool, then stirred at room temperature for 30 minutes and poured into water. The solution was basified to pH 8 with 2N sodium hydroxide solution, and then extracted with ethyl acetate. The extract was washed with water, dried over magnesium sulphate and the solvent evaporated under reduced pressure to afford a pale yellow oil which crystallised on standing. Recrystallisation from hexane gave 1-(2-amino-6-chloro-4-trifluoromethylphenyl)-3-tertiary-butyl-5-diethylamino-1,2,4-triazole (260mg).

Melting point : 97.5-98.5° C.

$^1$H NMR δ(CDCl$_3$): 7.06 (1H,s); 6.82 (1H,s); 4.32 (2H,s); 3.30 (2H,m); 3.08 (2H,m); 1.35 (9H,s); 1.02 (6H,t).

Step (b)

Concentrated sulphuric acid (600mg) was added to acetic acid (3ml), followed by sodium nitrite (150mg). The reaction mixture was stirred vigorously for 30 minutes, and then a solution of the amino-compound prepared in the preceding paragraph (260mg) in acetic acid (2ml) was added dropwise. After stirring at room temperature for 30 minutes the reaction mixture was added to a stirred solution of sodium cyanide (260mg), copper cyanide (260mg) and sodium acetate trihydrate (1.5gm) in water (5ml) at 5° C. After 10 minutes the reaction mixture was warmed to room temperature and stirred for a further 60 minutes. The reaction mixture was poured into water and basified to pH 9 by the addition of 2N sodium hydroxide. The reaction mixture was extracted with ethyl acetate and the extracts washed with water, dried over magnesium sulphate and the solvent evaporated under reduced pressure to give a brown oil (230mg). The desired compound was isolated by preparative HPLC using 10% ethyl acetate-hexane as eluent. The compound was an oil (50mg).

$\mu$max (film): 2220 cm$^{-1}$;

$^1$H NMR $\delta$(CDCl$_3$): 8.00 (1H,s); 7.30 (1H,s); 3.16 (4H,q); 1.35 (9H,s); 1.05 (6H,t).

EXAMPLE 8

The following examples illustrate the preparation of compounds according to the general method of Example 6.

(a) 1-(2-Cyano-6-fluoro-4-trifluoromethylphenyl)-4-pentafluoroethylpyrimidin-6-one (Compound No. 21 in Table I), from 1-(2-bromo-6-fluoro-4-trifluoromethylphenyl) -4-pentafluoroethylpyrimidin-6-one (from Preparation 21).

$^1$H NMR $\delta$(CDCl$_3$): 8.15 (1H,s); 7.99 (1H,s); 7.90 (1H,d); 7.08 (1H,s).

(b) 1-(2-Cyano-6-chloro-4-trifluoromethoxyphenyl)-4-pentafluoroethylpyrimidin-6-one (Compound No. 22 of Table I) from 1-(2-bromo-6-chloro-4-trifluoromethoxyphenyl)-4-pentafluoroethylpyrimidin-6-one (the product of Preparation 26).

$^1$H NMR $\delta$(CDCl$_3$) 8.09 (1H,s); 7.77 (1H,d); 7.65 (1H,d); 7.08 (1H,s)

EXAMPLE 9

This example illustrates the preparation of 1-(2-chloro-6-cyano-4-trifluoromethylphenyl)-3-dimethylamino-4-(trifluoromethylthio)pyrazole (Compound No. 23 of Table IV).

Step (a)

Benzyl chloroformate (4.8ml) was carefully added to a solution of 3-aminopyrazole (2.5g) in a mixture of dichloromethane (25ml) and triethylamine (5ml), giving a vigorous exotherm. The reaction mixture was stirred for two hours, poured into sodium bicarbonate and allowed to stand overnight. The organic layer was separated, washed with brine and dried over magnesium sulphate. Evaporation of the solvent under reduced pressure gave a pale yellow solid (4.5g). The solid was recrystallised from ethyl acetate to give benzyloxycarbonyl protected 3-aminopyrazole (1.9g).

$^1$H NMR $\delta$(CDCl$_3$): 7.89 (1H,d); 7.5-7.3 (5H,m); 5.86 (1H,d); 5.42 (2H,s); 4.02 (2H,broad s)

Step (b)

The protected pyrazole (1.37g) prepared in Step (a) was suspended in acetonitrile (25ml) and then 37% aqueous formaldehyde (5.5ml) was added. After stirring for 10 minutes sodium cyanoborohydride (1.2g) was added as a single portion, followed by dropwise addition of glacial acetic acid (0.7ml) over 10 minutes. The mixture was stirred at ambient temperature for two hours and then a second portion of acetic acid (0.7ml) was added. The mixture was stirred for a further 30 minutes, then ethyl acetate was added and the mixture poured into aqueous sodium bicarbonate. The organic layer was washed with aqueous sodium bicarbonate and brine and then dried over magnesium sulphate. Evaporation of the solvent under reduced pressure gave a colourless gum which was purified by column chromatography using diethyl ether as eluent. The product was a benzyloxycarbonyl-protected 3-dimethylaminopyrazole derivative (990mg).

$^1$H NMR $\delta$(CDCl$_3$): 7.90 (1H,d); 7.5-7.3 (5H,m); 5.9 (1H,d); 5.42 (2H,s); 2.95 (6H,s)

Step (c)

The protected dimethylaminopyrazole (1.42g) was dissolved in methanol (25ml) and a catalytic quantity of 5% palladium on carbon (100mg) was added. The reaction mixture was exposed to one atmosphere of hydrogen gas for 30 minutes, then filtered and the solvent removed under reduced pressure. The residue was taken up in diethyl ether and an ethanolic solution of hydrogen chloride was added until no further precipitate was formed. The precipitate was collected by filtration, washed with diethyl ether and re-dissolved in methanol. The solution was transferred to a round-bottomed flask. Evaporation of the methanol gave a residue which was dissolved in water and then basified with potassium carbonate. The solution extracted with dichloromethane and the organic layers collected and dried over magnesium sulphate. Evaporation of the solvent under reduced pressure gave 3-dimethylaminopyrazole (440mg) as a yellow gum.

$^1$H NMR $\delta$(CDCl$_3$) 7.39 (1H,d); 5.69 (1H,d); 2.88 (6H,s).

Step (d)

A solution of 3-dimethyl-aminopyrazole (440mg) in dimethylformamide (3ml) was added in small portions to a suspension of sodium hydride (160mg of a 60% suspension in mineral oil) in dimethylformamide (2ml). The reaction mixture was stirred until all effervescence had stopped and then it was added to a solution of 2-fluoro-3-chloro-5-trifluoromethylbenzonitrile (1g) in dimethylformamide (15ml) under a nitrogen atomsphere. After one hour of stirring the mixture was poured into brine and extracted with ethyl acetate. The extracts were washed with brine, dried over magnesium sulphate and the solvent evaporated under reduced pressure to give a yellow solid (910mg) which was purified by recrystallisation from hexane to give 1-(2-chloro-6-cyano-4-trifluoromethylphenyl)-3-dimethylaminopyrazole.

melting point: 115-116° C.

$^1$H NMR $\delta$(CDCl$_3$): 7.94 (1H,d); 7.90 (1H,d); 7.86 (1H,d); 6.03 (1H,d); 2.98 (6H,s)

Step (e)

The arylated dimethylaminopyrazole (250mg) was dissolved in a mixture of diethyl ether (3ml) and pyridine (65$\mu$l). This solution was added to a solution of trifluoromethylsulphonyl chloride (approximately 200mg) in diethylether (2ml) which had been cooled to −78° C. The reaction mixture was allowed to slowly warm to ambient temperature and then to stand for 4 days. The mixture was diluted with diethyl ether, washed with brine and dried over magnesium sulphate. Evaporation of the solvent under reduced pressure gave a residue which was purified by flash chromatography using hexane containing 10% by volume of diethyl ether as eluent to give the desired compound as a yellow oil (105mg).

$^1$H NMR $\delta$(CDCl$_3$): 7.98 (1H,d); 7.96 (1H,s); 7.94 (1H,d); 3.14 (6H,s).

EXAMPLE 10

The activity of the compounds of formula (I) was determined using a variety of pests. The pests were treated with a liquid composition containing 500 parts per million (ppm) by weight of the compound unless otherwise stated. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

TABLE V

| COMPOUND | RATE OF APPLICATION ppm | SPECIES MD | BG (see Table VI) | HV | SP |
|---|---|---|---|---|---|
| 1 | 500 | 9 | 9 | 0 | 5 |
| 2 | 500 | 9 | 9 | 0 | 9 |
| 3 | 500 | 9 | 9 | 0 | 0 |
| 4 | 500 | 9 | 9 | 9 | 9 |
| 5 | 100 | 9 | 9 | 0 | 9 |
| 6 | 500 | 9 | 9 | 9 | 9 |
| 9 | 500 | 9 | 9 | 0 | 0 |
| 10 | 500 | 9 | 5 | 0 | 0 |
| 11 | 500 | 9 | 9 | 0 | 9 |
| 12 | 500 | 9 | 9 | 5 | 0 |
| 13 | 500 | 9 | 9 | 5 | 5 |
| 14 | 500 | 9 | 9 | 9 | 0 |
| 15 | 100 | 9 | 5 | 0 | 9 |
| 16 | 500 | 9 | 9 | 5 | 9 |
| 17 | 500 | 9 | 9 | 0 | 0 |
| 18 | 500 | 9 | 5 | 0 | 0 |
| 19 | 500 | 9 | 9 | 9 | 9 |
| 20 | 500 | 0 | 0 | 0 | 9 |
| 23 | 500 | 9 | 9 | 9 | 5 |

TABLE VI

| CODE LETTERS | TEST SPECIES | SUPPORT MEDIUM/FOOD | TYPE OF TEST | DURATION (DAYS) |
|---|---|---|---|---|
| BG | *Blattella germanica* (Cockroach nymphs) | Plastic pot | Residual | 3 |
| MD | *Musca domestica* (houseflies-adults) | Cotton wool/ sugar | Contact | 1 |
| HV | *Heliothis virescens* (tobacco budworm-larvae) | Cotton leaf | Residual | 2 |
| SP | *Spodoptera exigua* (lesser armyworm-larvae) | Cotton leaf | Residual | 2 |

"Contact" test indicates that both pests and medium were treated and "Residual" test indicates that the medium was treated before infestation with the pests.

The results of the tests are presented in Table V for each of the compounds at the rate in parts per million given in the second column. The results indicate a grading of mortality designated as 9, 5 or 0 wherein 9 indicates 80-100% mortality, 5 indicates 50-79% mortality and 0 indicates less than 50% mortality.

Information regarding the pest species, the support medium or food, and the type and duration of the test is given in Table VI. The pest species is designated by a letter code.

In Table VI the pest organism used is designated by a letter code and the pest species, the support medium or food, and the type and duration of test is given.

EXAMPLES 11-29

Examples 11-29 illustrate formulations suitable for the application of compounds according to the invention. In the examples, the following ingredients are referred to by their Registered Trade Marks and have the composition as shown below.

| Registered Trade Mark | Composition |
|---|---|
| Synperonic NP8 | Nonylphenol-ethylene oxide condensate |
| Synperonic NP13 | |
| Synperonic OP10 | |
| Aromasol H | Alkylbenzene solvent |
| Solvesso 200 | Inert organic diluent |
| Keltrol | Polysaccharide |

EXAMPLE 11

This Example illustrates an emulsifiable concentrate composition which is readily convertible by dilution with water into a liquid preparation suitable for spraying purposes. The concentrate has the following composition:

| | % Weight |
|---|---|
| Compound | 25.0 |
| SYNPERONIC NP13 | 2.5 |
| Calcium dodecylbenzenenesulphonate | 2.5 |
| Methylcyclohexanone | 70 |

EXAMPLE 12

This Example illustrates an emulsifiable concentrate composition which is readily convertible by dilution with water into a liquid preparation suitable for spraying purposes. The concentrate has the following composition:

| | % Weight |
|---|---|
| Compound | 10.0 |
| SYNPERONIC NP13 | 4.0 |
| Calcium dodecylbenzenesulphonate | 6.0 |
| AROMASOL H | 50.0 |
| Methylcyclohexanone | 30.0 |

EXAMPLE 13

This Example illustrates a wettable powder composition which is readily convertible by dilution with water into a liquid preparation suitable for spraying purposes. The wettable powder has the following composition:

|  | % Weight |
| --- | --- |
| Compound | 10.0 |
| Silica | 5.0 |
| Sodium lignosulphonate | 5.0 |
| Sodium lauryl sulphate | 4.0 |
| Kaolinite | 76.0 |

EXAMPLE 14

This Example illustrates a wettable powder composition which is readily convertible by dilution with water into a liquid preparation suitable for spraying purposes. The wettable powder has the following composition:

|  | % Weight |
| --- | --- |
| Compound | 1.0 |
| Sodium lignosulphonate | 5.0 |
| Sodium lauryl sulphate | 2.0 |
| Kaolinite | 92.0 |

EXAMPLE 15

This Example illustrates a wettable powder composition which is readily convertible by dilution with water into a liquid preparation suitable for spraying purposes. The wettable power has the following composition:

|  | % Weight |
| --- | --- |
| Compound | 40.0 |
| Silica | 20.0 |
| Calcium lignosulphonate | 5.0 |
| Sodium lauryl sulphate | 2.0 |
| Kaolinite | 33.0 |

EXAMPLE 16

This Example illustrates a dusting powder which may be applied directly to plants or other surfaces and comprises 1% by weight of the compound of the invention, 2% by weight of silica and 97% by weight of talc.

EXAMPLE 17

This Example illustrates a concentrated liquid formulation suitable for application by ultra low volume techniques after mixing with paraffinic diluents.

|  | % Weight |
| --- | --- |
| Compound | 25.0 |
| N-methyl-2-pyrollidone | 50.0 |
| SOLVESSO 200 | 25.0 |

EXAMPLE 18

This Example illustrates a concentrated liquid formulation suitable for application by ultra low volume techniques after mixing with paraffinic diluents.

|  | % Weight |
| --- | --- |
| Compound | 10.0 |
| N-methyl-2-pyrollidone | 20.0 |
| SOLVESSO 200 | 70.0 |

EXAMPLE 19

This Example illustrates a liquid formulation suitable for application (undiluted) by ultra low volume techniques.

|  | % Weight |
| --- | --- |
| Compound | 10 |
| Cotton seed oil | 50 |
| Butyldiethoxol acetate | 40 |

EXAMPLE 20

This Example illustrates a capsule suspension concentrate which is readily convertible by dilution with water to form a preparation suitable for application as an aqueous spray.

|  | % Weight |
| --- | --- |
| Compound | 10.0 |
| Toluene di-isocyanate | 3.0 |
| Ethylenediamine | 2.0 |
| Polyvinyl alcohol | 2.0 |
| Bentonite | 1.5 |
| Di-hydroisopharone | 30.0 |
| Solvesso 200 | 10.0 |
| Polysaccharide (e.g. KELTROL) | 0.1 |
| Water | 41.4 |

EXAMPLE 21

This Example illustrates a capsule suspension concentrate which is readily convertible by dilution with water to form a preparation suitable for application as an aqueous spray.

|  | % Weight |
| --- | --- |
| Compound | 1.0 |
| Toluene di-isocyanate | 3.0 |
| Ethylenediamine | 2.0 |
| Polyvinyl alcohol | 2.0 |
| Bentonite | 1.5 |
| Di-hydroisopharone | 5.0 |
| Solvesso 200 | 2.0 |
| Polysaccharide (e.g. KELTROL) | 0.1 |
| Water | 83.4 |

EXAMPLE 22

This Example illustrates a ready for use granular formulation:

|  | % Weight |
| --- | --- |
| Compound | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 23

This Example illustrates an aqueous suspension concentrate.

|  | % Weight |
|---|---|
| Compound | 50.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 18.3 |

EXAMPLE 24

This Example illustrates a ready for use dust (D.P.) made from a concentrate.

|  | % Weight |
|---|---|
| Concentrate: | |
| Compound | 10 |
| Silica | 20 |
| Magnesium Carbonate | 70 |
| Dust Example containing 1% active ingredient: | |
| Above concentrate | 10 |
| Talc | 90 |

EXAMPLE 25

This Example illustrates a ready for use granule formulation.

|  | % Weight |
|---|---|
| Compound | 5 |
| Synperonic NP8 | 2 |
| Pumice granules (20/40 BS Mesh) | 93 |

EXAMPLE 26

This Example illustrates a water dispersible granule formulation.

|  | % Weight |
|---|---|
| Compound | 50 |
| Silica | 5 |
| Sodium lignosulphate | 10 |
| Sodium dioctylsulphosuccinate | 5 |
| Sodium acetate | 10 |
| Montmorillonite powder | 20 |

EXAMPLE 27

Tis Example illustrates an emulsifiable concentrate which is diluteable in water to form a liquid composition for spraying.

|  | % Weight |
|---|---|
| Compound | 50.0 |
| Span 40 | 0.8 |
| Tween 40 | 8.0 |
| Di-hydroisopharone | 30.0 |
| Solvesso 100 | 25.0 |

-continued

|  | % Weight |
|---|---|
| Water | 31.2 |

EXAMPLE 28

This Example illustrates an aerosol concentrate.

|  | % Weight |
|---|---|
| Compound | 1.0 |
| Methyl-isobutylketone | 50.0 |
| Solvesso 100 | 94.0 |

EXAMPLE 29

This Example illustrates an aerosol composition.

|  | % Weight |
|---|---|
| Aerosol concentrate (Example 28) | 5.0 |
| Colourless kerosene | 25.0 |
| Methylene chloride | 10.0 |
| Propellant* | 60.0 |

*(Hydrocarbon aerosol propellant, pressure 40–80 psig)

We claim:

1. A compound of formula (I):

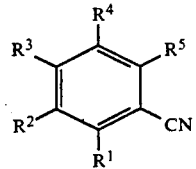

wherein $R^1$ is a group of sub-formula (b):

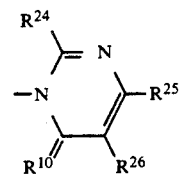

where $R^{10}$ is oxygen or sulphur; $R^{24}$ is hydrogen, halogen, $NR^7R^8$, $S(O)_nR^6$, lower alkyl or cycloalkyl having from 3 to 7 carbon atoms wherein $R^7$ and $R^8$ are independently selected from hydrogen, lower alkyl or cycloalkyl having from 3 to 7 carbon atoms; $R^{25}$ is halo, nitro, halo-lower alkyl, halo-lower alkoxy or $S(O)_nR^6$; and $R^{26}$ is hydrogen, alkyl, halogen, cyano, hydroxy-lower alkyl, lower alkxoy, $S(O)_nR^6$, halo-lower alkylthio, $NR^{11}R^{12}$ wherein $R^{11}$ and $R^{12}$ are independently selected from hydrogen or lower alkyl optionally substituted by $C_{2-5}$ alkoxycarbonyl, or cycloalkyl containing from 3 to 7 carbon atoms, formyl, nitro or halo-lower alkyl; $R^2$ is hydrogen, halogen, halo-lower alkyl, nitro or cyano; $R^3$ and $R^5$ are independently selected from hydrogen, halogen, lower alkyl or cycloalkyl having from 3 to 7 carbon atoms; $R^4$ is halogen, halo-lower alkyl, halo-lower alkoxy or $S(O)_nR^6$ where $R^6$ is lower alkyl, halo-lower alkyl or cycloalkyl having from 3 to 7 carbon atoms and n is 0, 1 or 2.

2. A compound according to claim 1 wherein $R^3$ and $R^5$ are independently selected from hydrogen or methyl.

3. A compound according to claim 1 or 2 wherein $R^2$ is fluorine, chlorine, bromine, cyano or trifluoromethyl.

4. A compound according to any one of the preceding claims wherein $R^4$ is selected from trifluoromethyl, pentafluoroethyl, $S(O)_nR^6$, iodine, bromine, chlorine or trifluoromethoxy.

5. Compound for formula (I) according to claim 1 wherein $R^2$ is hydrogen, halogen or cyano, $R^3$ and $R^5$ are independently hydrogen or lower alkyl, $R^4$ is halo-lower alkyl, halo-lower alkoxy or $S(O)_nR^6$ where $R^6$ is halo-lower alkyl or lower alkyl and n is 0, 1 or 2, and $R^1$ is pyrimidinone or pyrimidinthione of sub-formula (b)

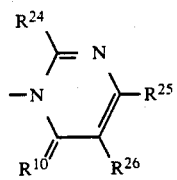

(b)

where $R^{10}$ is oxygen or sulphur; $R^{24}$ is hydrogen, $NR^7R^8$, lower alkyl or cycloalkyl, where $R^7$ and $R^8$ are hydrogen; $R^{25}$ is halo-lower alkyl; and $R^{26}$ is hydrogen, alkyl halogen, cyano, or $S(O)_nR^6$ where n and $R^6$ are as defined herein.

6. A method of killing or controlling insect or acarine pests which method comprises applying to the pest or to a locus thereof an effective amount of a compound of formula (I) as defined in claim 1.

7. An insecticidal or acaricidal composition comprising an effective amount of a compound of formula (I) as defined in claim 1 in combination with a diluent or carrier.

* * * * *